United States Patent [19]

Ballard et al.

[11] Patent Number: 4,745,237
[45] Date of Patent: May 17, 1988

[54] PREPARATION OF 1-CHLORO-1,2,2,2-TETRAFLUOROETHANE

[75] Inventors: Denis G. H. Ballard, Littleton; Jeffrey Farrar, Kelsall; Dale A. Laidler, Dee Banks, all of England

[73] Assignee: Imperial Chemical Industries PLC, London, England

[21] Appl. No.: 90,385

[22] Filed: Aug. 27, 1987

Related U.S. Application Data

[63] Continuation of Ser. No. 741,743, Jun. 6, 1985, abandoned.

[30] Foreign Application Priority Data

Jun. 14, 1984 [GB] United Kingdom ............... 8415201

[51] Int. Cl.$^4$ ............... C07C 17/00; C07C 17/38; C07C 19/02
[52] U.S. Cl. ............................. 570/176; 570/177
[58] Field of Search ............................. 570/176, 177

[56] References Cited

U.S. PATENT DOCUMENTS 2,920,112  1/1960  Larsen ........................ 260/653
4,319,060  3/1982  Cunningham et al. ........ 570/177

FOREIGN PATENT DOCUMENTS 1453510   8/1966  France ........................ 570/177
  55306   4/1983  Japan .......................... 423/657
 681067  10/1952  United Kingdom .

Primary Examiner—J. E. Evans
Attorney, Agent, or Firm—Cushman, Darby & Cushman

[57] ABSTRACT

A method for the preparation of 1-chloro-1,2,2,2-tetrafluoroethane which comprises treating 1,1-dichloro-1,2,2,2-tetrafluoroethane, optionally in the form of an isomer mixture, with an alkali metal amalgam in an active hydrogen containing liquid medium which includes a solvent for the dichlorotetrafluoroethane.

6 Claims, No Drawings

PREPARATION OF 1-CHLORO-1,2,2,2-TETRAFLUOROETHANE

This is a continuation of application Ser. No. 741,743, filed June 6, 1985 which was abandoned upon the filing hereof.

This invention relates to a chemical process and more particularly to a method for the preparation of 1-chloro-1,2,2,2-tetrafluoroethane.

1-Chloro-1,2,2,2,-tetrafluoroethane is a known chemical compound which is useful as a refrigerant, a heat pump working fluid, an aerosol propellant and a blowing agent. The methods that have been described for its preparation have not generally been suitable for industrial exploitation because of the poor yields obtained or the expensive starting materials used. The basis of some of these methods, for example Ger. Offen No. 3,009,760, is the hydrofluorination of chlorotrifluoroethylene and this route has been claimed to provide the required product in high yields. It suffers, however, from the disadvantages that chlorotrifluoroethylene is a costly starting material and that special plant is required for handling hydrogen fluoride.

Chlorotetrafluoroethanes have also been reported to be formed in the hydrogenolysis of dichlorotetrafluoroethanes which are made, as a mixture of the two isomers, by the reaction of carbon tetrachloride with hydrogen fluoride and chlorine over a chromia catalyst or the chlorofluorination of ethylene. Thus, our U.K. Patent No. 1578933 describes the hydrogenolysis of dichlorotetrafluoroethanes over a palladium-on-charcoal or palladium-on-alumina catalyst at temperatures in the range 225°–400° C. to give a product mixture containing tetafluoroethanes and chlorotetrafluoroethanes, the isomer ratio for the chlorotetrafluoroethanes not being disclosed. The same reaction has been reported by Gervasutti et al (J. Fluorine Chemistry, 19, 1, 1981) to give minor amounts of 1-chloro-1,2,2,2-tetrafluoroethane and its isomer.

A higher yield of 1-chloro-1,2,2,2-tetrafluoroethane has been claimed (U.S. Pat. No. 2,920,112) from the reduction of 1,1-dichloro-1,2,2,2-tetrafluoroethane using zinc and isopropanol at 140° C.

It has now been found that the desired chlorotetrafluoroethane can be produced in excellent yield from 1,1-dichloro-1,2,2,2-tetrafluoroethane by the action of an alkali metal amalgam under very mild conditions, for example at normal ambient temperatures or thereabouts.

Thus, according to the invention, there is provided a method for the preparation of 1-chloro-1,2,2,2-tetrafluoroethane which comprises treating 1,1-dichloro-1,2,2,2-tetrafluorethane with an alkali metal amalgam in an active hydrogen containing liquid medium which includes a solvent for the dichlorotetrafluoroethane.

The alkali metal amalgam used may be, for example, sodium amalgam which may be prepared in conventional manner by the electrolysis of an aqueous solution of sodium hydroxide or a sodium salt using a mercury cathode or by dissolving sodium in mercury. Suitable amalgams can contain from about 0.3% to about 1% by weight of sodium.

The active hydrogen containing reaction medium is or includes a compound having one or more labile hydrogens. Suitable reaction media include alcohols, for example lower alkanols such as methanol, ethanol and propanols, and aqueous alcohols. Aprotic solvents such as acetonitrile and dimethylformamide may be used in admixture with the active hydrogen containing compounds. Thus, the reaction medium may be a mixture of water and an aprotic solvent for the dichlorotetrafluoroethane, a surface active agent being employed when the solvent and water are immiscible.

The reaction is conveniently performed at temperatures in the range from −35° C. to 30° C., preferably in the range from 0° to 5° C. Since the reaction is exothermic, it will usually be necessary to cool the reaction mixture in order to maintain these temperatures. The pressure under which the reaction is performed is not important and, consequently, atmospheric pressure conditions will usually be employed.

The 1,1-dichloro-1,2,2,2-tetrafluoroethane used as starting material in the method of the invention may be the substantially pure compound or it may be used in the form of a commercially available mixture with 1,2,-dichloro-1,1,2,2-tetrafluoroethane. Using such isomer mixtures, it is possible to convert the 1,1-dichloro compound to 1-chloro-1,2,2,2-tetrafluoroethane in very high yield whilst leaving the 1,2-dichloro compound virtually unchanged. Suitable mixtures contain at least 1% and typically from 5 to 95% of the 1,1-dichloro compound on a molar basis.

Thus, according to a further feature of the invention, there is provided a method for increasing the 1,2-dichloro-1,1,2,2-tetrafluoroethane content of a mixture of dichlorotetrafluoroethane isomers which comprises treating said mixture with an alkali metal amalgam in an active hydrogen containing liquid medium which includes a solvent for the dichlorotetrafluoroethane. Mixtures of 1,1-dichloro-1,2,2,2-tetrafluoroethane and 1,2-dichloro-1,1,2,2-tetrafluoroethane are not otherwise normally separable by distillation because of the coincidence of their boiling points. Under optimum conditions, the 1,2,-dichloro1,1,2,2-tetrafluoroethane may be obtained in very high purity.

At the end of the reaction, the product and any unchanged starting materials may be separated by virtue of their different boiling points.

The invention is illustrated but not limited by the following Examples.

EXAMPLE 1

A multi-necked 250 ml round-bottomed flask was fitted with an efficient magnetic stirrer bar, a compensating dropping funnel, a means of introducing liquids through a rubber septum and a Drikold-acetone condenser held at −78° C. The condenser in turn was attached to an isolatable glass tube which was kept in a pentane-liquid nitrogen slush bath at −112° C. Into the round-bottomed flask were placed methanol (35.5 mls, 0.8726 moles) and distilled water (5.3 mls, 0.2944 moles). The whole apparatus was purged with nitrogen and the flask was cooled to 0° C. in an ice-bath. A mixture of 1,2-dichlorotetrafluoroethane and 1,1-dichlorotetrafluoroethane (4.0 mls, 0.0363 moles) was injected through the rubber septum. The isomeric composition of the mixture had previously been determined by $^{19}F$ nmr to be 48.8% 1,2-dichloro-(0.01772 moles) and 51.2% 1,1-dichloro-compound (0.01855 moles). The homogeneous aqueous alcohol and chlorofluorocarbon mixture was stirred efficiently and sodium amalgam (160.0g, 0.5 w/w %, 0.0348 moles Na) was added from the dropping funnel over 35 minutes and stirring under reflux was continued for a further 40 minutes. The Drikold-acetone mixture was removed from the condenser and the volatile unreacted starting materials and products were allowed to distil over into the pentane-liquid nitrogen cooled trap. The reaction flask was removed from the ice-bath and warmed gently to aid distillation of the volatiles. After 2.25 hours, the contents of the pentane-liquid nitrogen trap were transferred by evaporation into an evacuated volumetrically calibrated 5 liter flask which was then let down to atmospheric pressure. The contents of the flask were quantitatively analysed for residual starting materials and products by gas chromatography using a 14'×¼" Durapak Carbowax 400 on Porasil C glass column at 47° C. The identity of the products was confirmed by both gas chromatographic mass spectrometry and comparison of retention times with authentic samples. The analytical results are reported in the Table. At the conclusion of the experiment, dilute hydrochloric acid was added to the reaction flask. No gas was evolved by the mercury indicating, qualitatively at least, that all of the sodium present in the amalgam originally had been reacted.

EXAMPLE 2

The experimental apparatus and procedure were similar to those described in the previous Example except that the solvent mixture consisted of ethanol (51.2 mls, 0.8765 moles) and distilled water (5.25 mls, 0.2917 moles) and the sodium amalgam (160.0 g; 0.5 w/w %, 0.0348 moles Na) was added over 15 minutes. At the conclusion of the experiment, the products and unreacted starting materials were transferred to the calibrated 5 liter flask and analysed. The analytical data are recorded in the Table. When dilute hydrochloric acid was added to the reaction flask no gas was evolved by the mercury indicating, qualitatively at least, all of the sodium present in the amalgam originally had been reacted.

EXAMPLE 3

The experimental apparatus and procedure were similar to those described in Example 1 except that the solvent mixture comprised isopropanol (67.1 mls, 0.8765 moles) and distilled water (5.25 mls, 0.2917 moles). Sodium amalgam (160.0 g, 0.5 w/w %, 0.0348 moles Na) was added to the ice cold aqueous alcohol-chlorofluorocarbon mixture over 15 minutes and stirring under reflux was continued for a further 1.5 hours. The Drikold-acetone mixture was removed from the condenser and replaced by iced water so that the temperature of the condenser was within the range 0°-5° C. Hot water (ca 100 mls) was injected into the reaction flask through the rubber septum and the volatile starting materials and products distilled over into the pentane-liquid nitrogen cold trap. These materials were evaporated into the calibrated 5 liter flask and analysed chromatographically. The analytical data are recorded in the Table. When concentrated hydrochloric acid was added to the reaction flask at the conclusion of the experiment, considerable evolution of gas from the mercury was noted indicating that not all of the sodium present in the original amalgam had been consumed.

EXAMPLE 4

The experimental apparatus and procedure were similar to those described in the previous Examples. The previously described dichlorotetrafluoroethane isomer mixture was added to an ice-cold mixture of acetonitrile (46 mls, 0.8765 moles) and distilled water (5.25 mls, 0.2917 moles) to form a homogeneous mixture. Sodium amalgam (160.0 g, 0.5 w/w %, 0.0348 moles Na) was added dropwise over 10 minutes and stirring at 0° C. was continued for a further 3 hours. Reaction was very sluggish evidenced by the slow rate of reflux and the formation of two layers. After 3 hours, the Drikold-acetone mixture was removed from the condenser and replaced by iced water so that the temperature of the condenser was within the range 0°-5° C. Hot water (ca 100 mls) was injected into the reaction flask and the volatile fluorochlorocarbons distilled over into the pentane-liquid nitrogen cold trap. After 2.5 hrs, the condensed materials were evaporated into the calibrated 5 liter flask and analysed chromatographically. The analytical data are recorded in the Table. When concentrated hydrochloric acid was added to the reaction flask at the conclusion of the experiment, a vigorous evolution of gas from the mercury was noted indicating that not all of the sodium present in the original amalgam had been consumed.

EXAMPLE 5

Into a nitrogen purged 250 ml multinecked round-bottomed flask which was connected to a Drikold-acetone condenser at −78° C. and a magnetic follower was placed anhydrous methanol (48.1 mls, 1.187 moles). The flask was cooled to 0° C. in an ice-bath and a mixture of 1,2-dichlorotetrafluoroethane and 1,1dichlorotetrafluoroethane (5.0 mls, 0.0445 moles) was injected through a rubber septum. The isomeric composition of the mixture had previously been determined by $^{19}$F nmr to be 74.4% 1,2-dichloro (0.03309 moles) and 25.6% 1,1-dichloro compound (0.01138 moles). The homogeneous alcohol and chlorofluorocarbon mixture was stirred efficiently and sodium amalgam (100g; 0.5 w/w %, 0.022 moles Na) was added dropwise over 10 minutes. After a small quantity of amalgam had been added to the mixture, the deposition of sodium chloride from solution was noted. When the addition of the amalgam was complete, the ice-bath was removed from around the reaction flask and the solution was allowed to reflux for a further 1 hour. The contents of the Drikold-acetone reservoir were then removed and the volatile chlorofluorocarbon reactants and products were allowed to distil over with the aid of a slow nitrogen purge and were condensed into a receiver at −112° C. in a pentane-liquid nitrogen slush bath. After 1 hour, the contents of the receiver were transferred into an evacuated volumetrically calibrated 5 liter flask which was then let down to atmospheric pressure. The contents of the flask were quantitatively analysed for residual starting materials and products by gas chromatography using a 14'×¼" Durapak Carbowax 400 on Porasil C glass column at 47° C. The analytical results are reported in the Table. Dilute hydrochloric acid was added to the reaction flask at the conclusion of the experiment and the evolution of only a few bubbles of gas from the mercury indicated, qualitatively at least, that the bulk of the sodium originally in the amalgam had reacted.

EXAMPLE 6

The experimental apparatus and procedure were similar to those described in the previous Examples except that the solvent mixture comprised methanol (43.5 mls, 1.076 moles) and distilled water (6.4 mls, 0.358 moles). A 74.4:25.6 molar ratio mixture of 1,2-dichloro and 1,1-dichloro compounds (0.0445 moles in total) was used. During addition of amalgam to the homogeneous aqueous alcohol-chlorofluorocarbon mixture, sodium chloride was deposited from solution. Following distillation into the pentane-liquid nitrogen cold trap, the products and starting materials were transferred to the calibrated volumetric flask and analysed quantitatively. The analytical data is presented in the Table. When dilute hydrochloric acid was added to the reaction flask at the conclusion of the experiment, there was no gas evolution from the mercury indicating that all of the sodium originally in the amalgam had reacted.

EXAMPLE 7

The experimental apparatus and procedure were similar to those described in the previous Example except that the solvent mixture comprised methanol (30.0 mls, 0.742 moles) and distilled water (12.5 mls, 0.694 moles) A 74.4:25.6 molar ratio mixture of 1,2-dichloro and 1,1-dichloro compounds (0.0445 moles in total) was used and it was necessary to stir the aqueous alcohol and chlorofluorocarbon mixture efficiently to promote intimate mixing of the two phases. Following completion of the reaction in which the sodium chloride by-product remained in solution, the products and unconverted starting materials were transferred to the calibrated volumetric flask and analysed quantitatively. The analytical data are presented in the Table. When dilute hydrochloric acid was added to the reaction flask at the conclusion of the experiment, there was no evolution of gas from the mercury indicating that it had been totally stripped of all the sodium originally in the amalgam.

EXAMPLE 8

The experimental apparatus and procedure were similar to those described in the previous Examples with the exception that the solvent mixture comprised methanol (14.5 mls, 0.358 moles and distilled water (19.4 mls, 1.077 moles . A 74.5:25.6 molar ratio mixture of 1,2-dichloro- and 1,1-dichloro compounds (0.0445 moles in total) was used. The products and unconverted starting materials were collected and analysed quantitatively as described previously; the analytical results are presented in the Table. It was noted that when dilute hydrochloric acid was added to the reaction flask at the conclusion of the experiment, gas was evolved from the mercury indicating that removal of sodium from the amalgam was incomplete.

EXAMPLE 9

The experimental apparatus and procedure were similar to those described in the previous Example with the exception that the added diluent was distilled water (25.8 mls, 1.436 moles) alone. As in the previous Example, a 74.4:25.6 molar ratio mixture of 1,2-dichloro- and 1,1-dichloro compounds (0.0445 moles in total) was used and it was necessary to use an efficient stirring bar to promote satisfactory mixing of the aqueous and chlorofluorocarbon phases. At the conclusion of the experiment the volatile products and starting materials were transferred to the calibrated 5 liter flask and analysed. When dilute hydrochloric acid was added to the reaction flask, vigorous evolution of gas from the mercury occurred indicating, qualitatively at least, that there was a considerable quantity of unreacted sodium present in the amalgam.

EXAMPLE 10

The experimental apparatus and procedure were similar to those described in the previous Examples. Into the round-bottomed flask were placed methanol (106.5 mls, 2.618 moles) and distilled water (15.75 mls, 0.875 mole). The whole apparatus was purged with nitrogen and the flask was cooled to 0° C. in an ice-bath. A mixture of dichlorotetrafluoroethanes (19.157 g, 0.1121 moles) was injected through the rubber septum. The isomeric composition of the mixture had previously been determined by $^{19}F$ nmr to be 91.8% 1,2-dichloro (0.1029 moles) and 8.2% 1,1-dichloro compound (0.0092 moles). The homogeneous aqueous alcohol and chlorofluorocarbon mixture was stirred efficiently and sodium amalgam (83.18 g, 0.5 w/w 0.0179 moles Na) was added over 20 minutes. Stirring under reflux was continued for a further 2 hours after which the Drikold-acetone mixture was removed and the temperature of the condenser was adjusted to 0°–5° C. The volatile starting materials and products were distilled over into the pentane-liquid nitrogen cold trap and transferred to the calibrated 5 liter flask for analysis. The data are reported in the Table. When dilute hydrochloric acid was added to the reaction flask at the end of the reaction, no gas was evolved from the mercury indicating that, qualitatively a least, all of the sodium present in the original amalgam had been consumed.

In the Table, TFE=tetrafluoroethylene and CTFE=chlorotrifluoroethylene, ND=not detected.

TABLE

| EXAMPLE | SOLVENT MIXTURE (MOLAR RATIO) | 1,2-DICHLORO/ 1,1-DICHLORO RATIO | INITIAL TOTAL CONCN. (MOLES) | CONVERSION (%) | | PRODUCT YIELDS (MOLES) | | | PRODUCT SELECTIVITIES (%) | | |
|---|---|---|---|---|---|---|---|---|---|---|---|
| | | | | $CF_2ClCF_2Cl$ | $CF_3CFCl_2$ | TFE | CTFE | $CF_3CFClH$ | TFE | CTFE | $CF_3CFClH$ |
| 1 | MeOH—H$_2$O (74.7:25.3) | 48.8:51.2 | 0.0363 | 3.4 | 90.3 | 0.00123 | 0.00005 | 0.01598 | 7.1 | 0.3 | 92.5 |
| 2 | EtOH—H$_2$O (75.0:25.0) | 48.8:51.2 | 0.0363 | 2.2 | 87.1 | 0.00056 | 0.00009 | 0.01476 | 3.6 | 0.6 | 95.8 |
| 3 | i-PrOH—H$_2$O (75.0:25.0) | 48.8:51.2 | 0.0363 | 0.5 | 32.3 | 0.00021 | 0.00024 | 0.00462 | 4.1 | 4.8 | 91.1 |
| 4 | MeON—H$_2$O (74.9:25.1) | 48.8:51.2 | 0.0363 | 0.3 | 27.6 | 0.00017 | 0.00052 | 0.00449 | 3.4 | 10.1 | 86.5 |
| 5 | MeOH (100) | 74.4:25.6 | 0.0445 | 10.4 | 74.3 | 0.00188 | N.D. | 0.00519 | 26.6 | 0 | 73.4 |
| 6 | MeOH—H$_2$O (75.0:25.0) | 74.4:25.6 | 0.0445 | 11.6 | 73.4 | 0.00110 | 0.00008 | 0.00657 | 14.2 | 1.0 | 84.8 |
| 7 | MeOH—H$_2$O (51.7:48.3) | 74.4:25.6 | 0.0445 | 11.7 | 73.7 | 0.00203 | 0.00021 | 0.00606 | 24.5 | 2.5 | 73.0 |
| 8 | MeOH—H$_2$O (24.9:75.1) | 74.4:25.6 | 0.0445 | 1.0 | 15.2 | 0.00093 | 0.00011 | 0.00134 | 39.2 | 4.5 | 56.3 |
| 9 | H$_2$O | 74.4:25.6 | 0.0445 | 6.0 | 0 | 0.00199 | ND | ND | 100 | 0 | 0 |

TABLE-continued

| EXAMPLE | SOLVENT MIXTURE (MOLAR RATIO) | 1,2-DICHLORO/ 1,1-DICHLORO RATIO | INITIAL TOTAL CONCN. (MOLES) | CONVERSION (%) | | PRODUCT YIELDS (MOLES) | | | PRODUCT SELECTIVITIES (%) | | |
|---|---|---|---|---|---|---|---|---|---|---|---|
| | | | | $CF_2ClCF_2Cl$ | $CF_3CFCl_2$ | TFE | CTFE | $CF_3CFClH$ | TFE | CTFE | $CF_3CFClH$ |
| 10 | (100) MeOH—$H_2O$ (74.9:25.1) | 91.8:8.2 | 0.1121 | 4.9 | 91.4 | 0.00065 | 0.00007 | 0.00439 | 12.7 | 1.4 | 86.9 |

We claim:

1. A method for the selective preparation of 1-chloro-1,2,2,2-tetrafuoroethane which comprises treating a mixture of 1,1-dichloro-1,2,2,2-tetrafluoroethane and 1,2-dichloro-1,1,2,2-tetrafluoroethane at a temperature in the range form −35° to 30° C. with an alkali metal amalgam in an active hydrogen containing liquid medium which includes a solvent for the dichlorotetrafluoroethanes and separating the 1-chloro-1,2,2,2-tetrafluoroethane from unchanged 1,2-dichloro-1,1,2,2-tetrafluoroethane.

2. A method according to claim 1 wherein the alkali metal amalgam is sodium amalgam.

3. A method according to claim 1 wherein the active hydrogen containing liquid medium is an alcohol.

4. A method according to claim 1 wherein the active hydrogen containing liquid medium is an aqueous alcohol.

5. A method according to claim 1 wherein the active hydrogen containing liquid medium is a mixture of water and an aprotic solvent for the dichlorotetrafluoroethane.

6. A method according to claim 1 wherein the treatment is effected at a temperature in the range from 0° to 5° C.

* * * * *